United States Patent [19]

Carson

[11] Patent Number: 4,575,514
[45] Date of Patent: Mar. 11, 1986

[54] ANXIETY ALLEVIATING COMPOSITIONS CONTAINING LOWERALKYL-N-[AMINO(ARYLAMINOCARBONYL)-IMINOMETHYL]-N-METHYLGLYCINATES

[75] Inventor: John R. Carson, Norristown, Pa.

[73] Assignee: McNeilab, Inc., Fort Washington, Pa.

[21] Appl. No.: 670,654

[22] Filed: Nov. 9, 1984

Related U.S. Application Data

[62] Division of Ser. No. 450,827, Dec. 20, 1982, abandoned.

[51] Int. Cl.[4] ............... A61K 31/215; C07C 101/453
[52] U.S. Cl. ........................................ 514/542; 560/34

[58] Field of Search ............... 560/34; 424/309; 514/542

[56] References Cited

U.S. PATENT DOCUMENTS 4,060,635 11/1977 Diamond et al. ............... 424/322
4,204,000 5/1980 Diamond et al. ............... 424/304
4,353,842 10/1982 Diamond et al. ............... 560/34 X Primary Examiner—Bernard Helfin
Attorney, Agent, or Firm—David J. Levy

[57] ABSTRACT

Compounds of the class of loweralkyl N-[amino(arylaminocarbonyl)iminomethyl]-N-methylglycinate acid addition salts are useful as antianxiety agents.

18 Claims, No Drawings

ANXIETY ALLEVIATING COMPOSITIONS CONTAINING LOWERALKYL-N-[AMINO(ARYLAMINOCARBONYL)-IMINOMETHYL]-N-METHYLGLYCINATES

This application is a division of U.S. Ser. No. 450,827 filed Dec. 20, 1982, now abandoned.

This invention relates to loweralkyl N-[amino(arylaminocarbonyl)iminomethyl]-N-methylglycinate acid addition salts (I) which are useful as antianxiety agents.

DESCRIPTION OF PREFERRED EMBODIMENTS

The novel loweralkyl N-[amino(arylaminocarbonyl)iminomethyl]-N-methylglycinates in the form of their acid addition salts may be structurally represented by the following formula:

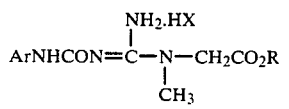

wherein Ar is phenyl substituted in the 3-position by a radical selected from the group consisting of halo, methoxy, methyl, ethyl, or trifluoromethyl; R is lower alkyl; and HX is a pharmaceutically acceptable strong acid. Typical examples of suitable acid addition salts include: HCl, $H_2SO_4$, $CH_3SO_3H$, p-tolyl—$SO_3H$, $H_3PO_4$ and the like.

As used herein, "loweralkyl" may be straight or branched chain and have from 1 to about 8 carbon atoms, such as, for example, methyl, ethyl, propyl, isopropyl, butyl, pentyl, octyl and the like alkyls. The term "halo" is generic to fluoro, bromo, chloro, and iodo.

The compounds of Formula I are prepared by the following two step process [which is depicted in Reaction Scheme A, below]:

(1) Reaction of arylisocyanate of Formula II with a soluble salt, for example, a tetralkylammonium salt or trialkylaralkylammonium ($Z^+$) salt such as, for example, tetrabutylammonium salt or benzyltrimethylammonium salt of creatine III to give an N-[amino(arylaminocarbonyl)iminomethyl]-N-methylglycine of Formula IV following acidification. This reaction is preferably conducted in an anhydrous, polar, inert, aprotic solvent such as, for example, DMF, DMSO, HMPA, tetramethylurea, THF, dioxane, DME, ethyl acetate and the like.

(2) Fischer esterification of the compound of Formula IV in an anhydrous lower alkanol such as, for example, methanol, ethanol, 2-propanol, 1-butanol and the like in the presence of excess strong acid such as, for example, HCl, $H_2SO_4$, $CH_3SO_3H$, p-tolyl-$SO_3H$, $H_3PO_4$ and the like.

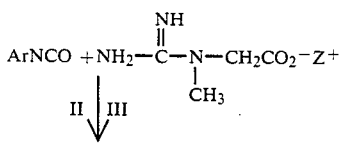

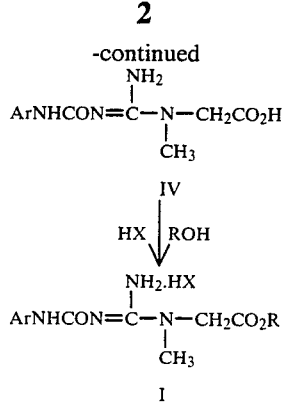

The compounds of Formula I have been found to possess useful CNS depressant properties, particularly antianxiety effects, by the following test indicative of such activities on laboratory animals, with the results shown in Table I, below.

The antianxiety assay was conducted by the procedure reported by I. Geller in *Psychosomatic Medicine*, J. H. Wodine and J. H. Moyer, Eds., Lea and Febiger, Philadelphia, 1962, p. 267. The antianxiety activity of the compound to be tested is studied in rats after intraperitoneal injection of the compound at doses generaly ranging from 10–25 mg/kg body weight and the effect of the compound on nonpunished and punished responses determined. Hungry rats are trained to press a bar for a food reinforcement: a dipper full of milk is delivered to the rat on the average of one every two minutes (variable interval schedule-V.I. II). Following 12 minutes on this schedule, a tone is presented for three minutes which signals the rewarding and simultaneous punishment of each bar press (a dipper full of milk is presented and accompanied by a shock, delivered through the grid floor, with each bar press). The shock delivered is 0.2 seconds in duration and ranges in intensity from 0.5–3.5 milliamperes. Each rat is presented with six alternating pairs of nonpunished periods when milk alone is given and punished periods when milk and shock are administered. Control responses are obtained for each rat after a saline intraperitoneal injection on the two days immediately preceding the compound treatment day. Each rat is evaluated at the same time of day and in the same test chamber. Responses are recorded and reinforcements (milk) and punishment (shock) were delivered by means of suitable automated equipment.

Each rat served as its own control in assessing the statistical significance of the effects of the test compound on nonpunished and punished responses respectively. The average of the total nonpunished and punished responses, respectively, observed on the two saline treatment days immediately preceding the test compound treatment day was compared to the total unpunished and the total punished responses, respectively, observed on the test compound treatment day. The statistical significance of the difference observed between the nonpunished responses and the punished responses, respectively, observed on the saline treatment day and the test compound treatment day was the t-test for paired observations.

TABLE I

| Compound | Dose mg/kg ip | N* | Nonpunished C** | Nonpunished TC*** | Punished C | Punished TC |
|---|---|---|---|---|---|---|
| I, R=$C_2H_5$ | 15 | 7 | 1795 | 1290 | 2.3 | 25.1s |

TABLE I-continued

| Compound | Dose mg/kg ip | N* | Mean Responses | | | |
|---|---|---|---|---|---|---|
| | | | Nonpunished | | Punished | |
| | | | C** | TC*** | C | TC |
| I, R=CH$_3$ | 25 | 6 | 3604 | 2137s | 2.1 | 21.8s |
| I, R=CH(CH$_3$)$_2$ | 25 | 8 | 1785 | 1325 | 2.4 | 12.0s |

N* Number of rats
C** Control
TC*** Test Compound
S Significantly different from control P < 0.05

In view of the foregoing, an effective CNS depressant amount of a compound of Formula I intimately admixed with a pharmaceutically acceptable carrier may be systemically administered to warm-blooded animals, including humans, to elicit a CNS depressant (anxiety alleviating) response. When administering the hereinabove described dosage unit forms for such purpose, amounts of active ingredient ranging about 15–500 mg, and preferably about 15–250 mg, per dosage unit may be utilized which may be administered orally or parenterally three or four times a day.

The preferred compounds of the present invention are those of Formula I wherein Ar is 3-chlorophenyl and R is C$_{1-3}$ lower alkyl.

The following examples are intended to illustrate and not limit the scope of the present invention. Example 1 illustrates the preparation of the intermediate of Formula IV, while the other examples illustrate preparing the final products of Formula I.

EXAMPLE 1

N-{Amino[(3-chlorophenyl)aminocarbonyl]iminomethyl}-N-methylglycine

A solution of 9.58 g (0.073 mole) of anhydrous creatine in 96 ml (0.073 mole) of 0.76M tetrabutylammonium hydroxide in methanol was evaporated to an oil in vacuo. The residue was dissolved in 100 ml of DMF. An 11.2 g (0.073 mole) sample of m-chlorophenylisocyanate was added dropwise and the reaction was stirred for two hours. The mixture was poured into 200 ml of water and 73 ml of 1N HCl. The gummy precipitate was induced to crystallize by scratching. The solid was collected and triturated with tetrahydrofuran to give 6.6 g (30% yield) of light yellow solid N-{amino[(3-chlorophenyl)aminocarbonyl]iminomethyl}-N-methylglycine. A hydrochloride salt was prepared from conc. HCl to yield a pink solid, m.p. 228°–234° C.

Anal. Calcd. for C$_{11}$H$_{12}$N$_4$O$_3$.HCl: C, 41.13; H, 4.39; N, 17.44. Found: C, 41.11; H, 4.47; N, 17.46. NMR (DMSO d$_6$+TFA) δ11.4 (1H, s); 9.1 (2H, s); 7.65–7.08 (4H, m), 4.5 (2H, s), 3.2 (3H, s).

EXAMPLE II

Methyl N-{Amino[(3-chlorophenyl)aminocarbonyl]iminomethyl}-N-methylglycinate hydrochloride A solution of 5.0 g of N-{amino[(3-chlorophenyl)aminocarbonyl]iminomethyl}-N-methylglycine in 50 ml of 5% methanolic hydrogen chloride was allowed to stand at room temperature for four hours. The white crystalline methyl N-{amino[(3-chlorophenyl)aminocarbonyl]iminomethyl}-N-methylglycinate hydrochloride was collected by filtration; 3.2 g (57% yield), m.p. 177° C. (d).

Anal. Calcd. for C$_{12}$H$_{14}$N$_4$O$_3$.HCl: C, 43.00; H, 4.81; N, 16.71. Found: C, 43.01; H, 4.84; N, 16.80. NMR (DMSO d$_6$+TFA) δ11.71 (1H, s), 7.4 (4H, m); 4.6 (2H, s), 3.75 (3H, s); 3.2 (3H, s).

EXAMPLE III

Ethyl N-{amino[(3-chlorophenyl)aminocarbonyl]iminomethyl}-N-methylglycinate hydrochloride A 6.6 g sample of N-{amino[(3-chlorophenyl)aminocarbonyl]iminomethyl}-N-methylglycine was dissolved in 350 ml of 2% ethanolic hydrogen chloride and allowed to stand at room temperature for 16 hours. The solution was cooled and the precipitated solid collected. A second crop of crystals was taken by concentration of the filtrate. The combined solids were washed with THF and recrystallized from 2% ethanolic hydrogen chloride to give 3.8 g (48% yield) of white crystalline ethyl N-{amino[(3-chlorophenyl)aminocarbonyl]iminomethyl}-N-methylglycinate, m.p. 171°–172° C.

EXAMPLE IV

2-Propyl N-{Amino[(3-chlorophenyl)aminocarbonyl]iminomethyl}-N-methylglycinate hydrochloride A 5.0 g sample of N-{amino[(3-chlorophenyl)aminocarbonyl]iminomethyl}-N-methylglycine was stirred in 200 ml of 4% hydrogen chloride in 2-propanol for 30 minutes. The undissolved solid was removed by filtration. The filtrate was stirred for 24 hours at 25°. The solution was cooled and the precipitated white crystalline 2-propyl N-{amino[(3-chlorophenyl)aminocarbonyl]iminomethyl}-N-methylglycinate, 3.5 g (55% yield), was collected and dried, m.p. 185° C. (d).

EXAMPLES V–XIV

By following the procedure of Example I, but substituting an equivalent amount of an appropriate arylisocyanate for the m-chlorophenylisocyanate used therein, and then by following the procedure of the appropriate one of Examples II–IV (as indicated), the following respective products may be prepared:

| Example | Compound | Example followed |
|---|---|---|
| V | Methyl N—{amino[(3-bromophenyl)aminocarbonyl]iminomethyl}-N—methylglycinate hydrochloride | 2 |
| VI | Methyl N—{amino[(3-iodophenyl)aminocarbonyl]iminomethyl}-N—methylglycinate hydrochloride | 2 |
| VII | Methyl N—{amino[(3-methoxyphenyl)aminocarbonyl]iminomethyl}-N—methylglycinate hydrochloride | 2 |
| VIII | Methyl N—{amino[(3-methylphenyl)aminocarbonyl]iminomethyl}-N—methylglycinate hydrochloride | 2 |
| IX | Methyl N—{amino[(3-ethylphenyl)aminocarbonyl]iminomethyl}-N—methylglycinate hydrochloride | 2 |
| X | Methyl N—{amino[(3-trifluoromethylphenyl)aminocarbonyl]iminomethyl}-N—methylglycinate hydrochloride | 2 |
| XI | Ethyl N—{amino[(3-fluorophenyl)aminocarbonyl]iminomethyl}-N—methylglycinate hydrochloride | 3 |
| XII | Ethyl N—{amino[(3-methylphenyl)aminocarbonyl]iminomethyl}-N—methylglycinate hydrochloride | 3 |
| XIII | Propyl N—{amino[(3-methoxyphenyl)aminocarbonyl]iminomethyl}-N—methylglycinate hydrochloride | 4 |
| XIV | Propyl N—{amino[(3-ethylphenyl)amino- | 4 |

| Example | Compound | Example followed |
|---|---|---|
| | carbonyl]iminomethyl}-N—methylglycinate hydrochloride | |

I claim:

1. A pharmaceutical useful against anxiety composition comprising an anxiety-alleviating amount of an acid addition salt compound of a loweralkyl N-[amino(arylaminocarbonyl)iminomethyl]-N-methylglycinate represented by the following formula (I):

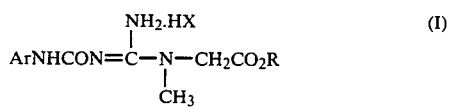

wherein
- Ar is phenyl substituted in the 3-position by a radical selected from the group consisting of halo, methoxy, methyl, ethyl or trifluoromethyl;
- R is lower alkyl; and
- HX is a pharmaceutically acceptable strong acid, and a pharmaceutically acceptable carrier.

2. The composition of claim 1, wherein in said compound of formula (I), Ar is 3-chlorophenyl and R is $C_{1-3}$ lower alkyl.

3. The composition of claim 1, wherein said compound is methyl N-[amino-[(3-chlorophenyl)aminocarbonyl]iminomethyl]-N-methylglycinate hydrochloride.

4. The composition of claim 1, wherein said compound is ethyl N-[amino[(3-chlorophenyl)aminocarbonyl]iminomethyl]-N-methylglycinate hydrochloride.

5. The composition of claim 1, wherein said compound is 2-propyl N-[amino[(3-chlorophenyl)aminocarbonyl]iminomethyl]-N-methylglycinate hydrochloride.

6. The composition of claim 1, wherein said compound is methyl N-(amino[(3-bromophenyl)aminocarbonyl]iminomethyl)-N-methylglycinate hydrochloride.

7. The composition of claim 1, wherein said compound is methyl N-(amino[(3-iodophenyl)aminocarbonyl]iminomethyl)-N-methylglycinate hydrochloride.

8. The composition of claim 1, wherein said compound is methyl N-(amino[(3-methoxyphenyl)aminocarbonyl]iminomethyl)-N-methylglycinate hydrochloride.

9. The composition of claim 1, wherein said compound is methyl N-(amino[(3-methylphenyl)aminocarbonyl]iminomethyl)-N-methylglycinate hydrochloride.

10. The composition of claim 1, wherein said compound which is methyl N-(amino[(3-ethylphenyl)aminocarbonyl]iminomethyl)-N-methylglycinate hydrochloride.

11. The composition of claim 1, wherein said compound is methyl N-(amino[(3-trifluoromethylphenyl)aminocarbonyl]iminomethyl)N-methylglycinate hydrochloride.

12. The composition of claim 1, wherein said compound is ethyl N-(amino[(3-fluorophenyl)aminocarbonyl]iminomethyl)-N-methylglycinate hydrochloride.

13. The composition of claim 1, wherein said compound is ethyl N-(amino[(3-methylphenyl)aminocarbonyl]iminomethyl)-N-methylglycinate hydrochloride.

14. The composition of claim 1, wherein said compound is propyl N-(amino[(3-methoxyphenyl)aminocarbonyl]iminomethyl)-N-methylglycinate hydrochloride.

15. The composition of claim 1, wherein said compound is propyl N-(amino[(3-ethylphenyl)aminocarbonyl]iminomethyl)-N-methylglycinate hydrochloride.

16. A method of alleviating the anxiety of a warm-blooded animal in need thereof which comprises administering to the animal, an anxiety-alleviating amount of the pharmaceutical composition of claim 1.

17. The method of claim 16, wherein said animal is a human.

18. The method of claim 16, wherein in said compound of formula (I), Ar is 3-chlorophenyl and R is $C_{1-3}$ loweralkyl.

* * * * *